United States Patent [19]
Catz et al.

[11] Patent Number: 5,238,933
[45] Date of Patent: Aug. 24, 1993

[54] SKIN PERMEATION ENHANCER COMPOSITIONS

[75] Inventors: Paul G. Catz, Palo Alto; David R. Friend, Menlo Park; Harold W. Nolen, III, San Jose, all of Calif.

[73] Assignee: SRI International, Menlo Park, Calif.

[21] Appl. No.: 862,387

[22] Filed: Apr. 2, 1992

Related U.S. Application Data

[63] Continuation-in-part of Ser. No. 783,480, Oct. 28, 1991.

[51] Int. Cl.⁵ ............................................. B01J 21/08
[52] U.S. Cl. .................................. 514/236.2; 514/423;
514/468; 514/947; 514/785; 514/582
[58] Field of Search ...................... 424/448, 449, 443;
514/946, 947, 236.2, 423, 468, 785, 582

[56] References Cited

U.S. PATENT DOCUMENTS

| | | | |
|---|---|---|---|
| 4,832,954 | 5/1989 | Sato et al. | 514/947 |
| 4,940,586 | 7/1990 | Cheng et al. | 424/449 |
| 5,028,435 | 7/1991 | Katz et al. | 424/484 |

*Primary Examiner*—Thurman K. Page
*Assistant Examiner*—Leon R. Horne
*Attorney, Agent, or Firm*—Dianne E. Reed

[57] ABSTRACT

Skin permeation enhancer compositions are provided which increase the permeability of skin to transdermally administered pharmacologically active agents. The compositions contain a lower aliphatic ester of a lower aliphatic carboxylic acid such as ethyl acetate and a lower alkanol such as propylene glycol. Methods and transdermal drug delivery systems for using the compositions are also provided.

32 Claims, 8 Drawing Sheets

SKIN PERMEATION ENHANCER COMPOSITIONS

CROSS-REFERENCE TO RELATED APPLICATIONS

This application is a continuation-in-part of pending U.S. Ser. No. 07/783,480, filed Oct. 28, 1991.

TECHNICAL FIELD

The present invention relates generally to the transdermal administration of pharmacologically active agents, and more particularly relates to compositions and methods for enhancing the permeability of the skin to such agents. The invention additionally relates to transdermal systems for drug administration, wherein the system is manufactured so as to contain a permeation enhancer composition as will be described herein.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences——e.g., gastrointestinal irritation and the like——are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10-15 microns thick over most of the body.

In order to increase skin permeability, and in particular to increase the permeability of the stratum corneum (i.e., so as to achieve enhanced penetration, through the skin, of the drug to be administered transdermally), the skin may be pretreated with a penetration enhancing agent (or "permeation enhancer", as sometimes referred to herein) prior to application of a drug. Alternatively, and preferably, a drug and a permeation enhancer are delivered concurrently.

The present invention is directed to a novel composition for enhancing the penetration of pharmacologically active agents through skin, the composition based on (1) a lower aliphatic ester of a lower aliphatic carboxylic acid with (2) a lower alkanol. The enhancer compositions of the invention have been found by the inventors herein to be particularly effective in enhancing the penetration of pharmaceutically active agents through skin, and surprisingly more effective than either component of the composition when used alone.

While there are a number of patents and publications available which relate to the transdermal administration of drugs and to skin permeation enhancer compositions, applicants are unaware of any art which suggests that the combinations now disclosed herein provide a synergistic enhancing effect.

RELATED ART

The following references relate to one or more aspects of the present invention.

Skin permeation enhancers, generally: Various compounds for enhancing the permeability of skin are known in the art. U.S. Pat. Nos. 4,006,218, 3,551,554 and 3,472,931, for example, respectively describe the use of dimethylsulfoxide (DMSO), dimethyl formamide (DMF) and N,N-dimethylacetamide (DMA) to enhance the absorption of pharmacologically active agents through the stratum corneum. Other compounds which have been used to enhance skin permeability include: decylmethylsulfoxide ($C_{10}MSO$); diethylene glycol monoethyl ether; polyethylene glycol monolaurate (PEGML; see, e.g., U.S. Pat. No. 4,568,343 to Leeper et al.); glycerol monolaurate (U.S. Pat. No. 4,746,515 to Cheng et al.); propylene glycol monolaurate (e.g., U.S. Pat. No. 4,764,379 to Sanders et al.); ethanol (e.g., as in U.S. Pat. No. 4,379,454 to Campbell et al.); eucalyptol (U.S. Pat. No. 4,440,777); lecithin (U.S. Pat. No. 4,783,450); the 1-substituted azacycloheptan-2-ones, particularly 1-n-dodecylcyclazacycloheptan-2-one (available under the trademark Azone® from Nelson Research & Development Co., Irvine, CA; see U.S. Pat. Nos. 3,989,816, 4,316,893, 4,405,616 and 4,557,934); "cell envelope disordering compounds" such as methyl laurate or oleic acid in combination with N-(hydroxyethyl) pyrrolidone (U.S. Pat. No. 4,537,776 to Cooper) $C_3$-$C_4$ diols (U.S. Pat. No. 4,552,872 to Cooper et al., European Patent Application Publication No. 043738); or a binary system of oleic acid, oleins or oleyl alcohol in combination with a lower alcohol (U.S. Pat. No. 4,863,970 to Chang et al.).

References which relate to lower aliphatic esters of lower aliphatic carboxylic acids or lower alkanols: European Pat. Publication No. 261,429, which describes the use of propylene glycol in combination with a fatty acid such as linoleic acid; U.S. Pat. No. 4,573,996 to Kwiatek et al., which describes the use of glycols in transdermal formulations; and U.S. Pat No 4,781,926 to Hyon et al., which describes transdermal formulations containing either ethyl acetate or propylene glycol as a permeation enhancer.

References which relate to drug-specific transdermal systems: U.S. Pat. No. 4,752,478 to Bondi et al. and U.S. patent No. 4,938,759 to Enscore et al. describe systems for the transdermal administration of timolol base; U.S. Pat. Nos. 4,560,553 to Zupan, 4,440,777 to Zupan and 4,990,340 to Hidaka all describe pharmaceutical preparations formulated with timolol maleate. PCT published patent application Nos. W088/09676 and U.S. Pat. No. 4,806,341 to Chien et al. relate to the transdermal administration of buprenorphine, while U.S. Pat. No. 4,573,995 to Chen et al. describes a system for the transdermal administration of nalbuphine.

SUMMARY OF THE INVENTION

Accordingly, it is a primary object of the present invention to provide a novel skin permeation enhancer composition comprising a lower aliphatic ester of a lower aliphatic carboxylic acid in combination with a lower alkanol.

Thus, in one embodiment, this invention comprises an admixture of a pharmacologically active agent plus the aforementioned permeation enhancer composition for the administration of therapeutically effective amounts of active agent.

In another embodiment, the invention is a method for enhancing the rate of penetration of a pharmacologically active agent through the skin, wherein the method comprises administering to the skin of the patient undergoing treatment a mixture of the pharmacologically active agent and the permeation enhancer composition as described herein.

In still another embodiment, the invention comprises a drug delivery device in the form of a laminated composite for administering a pharmacologically active agent through a selected area of skin. The device is preferably in the form of a laminated composite which includes a drug reservoir layer containing both the agent to be administered and the permeation enhancer composition of the invention.

DETAILED DESCRIPTION OF THE INVENTION

Figure 1:
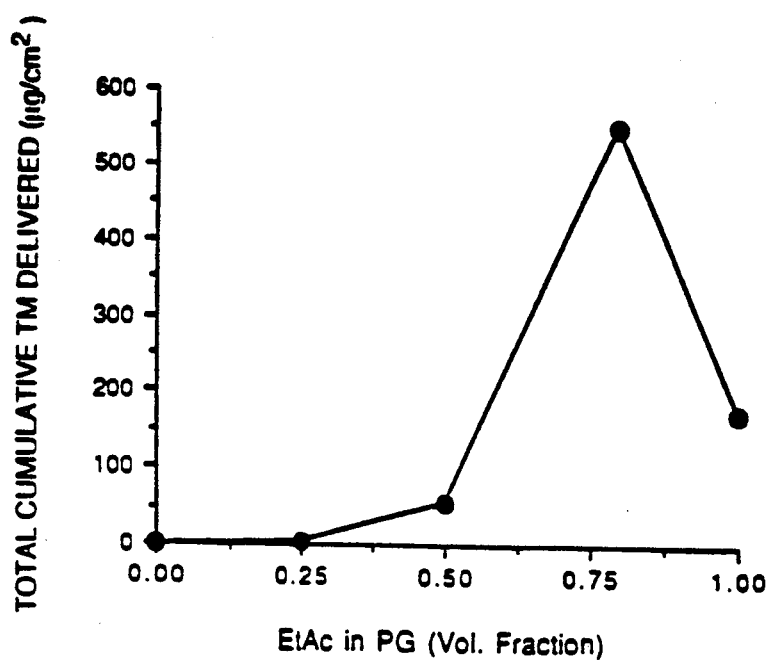
FIG. 1 graphically illustrates the cumulative amount of timolol maleate permeating though human skin over a 24 hour period using the enhancer compositions of the invention, as described in Example 1.

Before describing the present compositions, systems and methods of the invention in detail, it is to be understood that this invention is not limited to the particular drugs, transdermal devices or laminate materials described herein as such may, of course, vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the content clearly dictates otherwise. Thus, for example, reference to a laminated structure containing "a drug" includes a mixture of two or more drugs, reference to "a lower aliphatic ester" includes reference to one or more of such esters, reference to "a lower alkanol" includes reference to one or more lower alkanols, and the like.

In describing and claiming the present invention, the following terminology will be used in accordance with the definitions set out below.

"Penetration enhancement" or "permeation enhancement" as used herein relates to an increase in the permeability of skin to a pharmacologically active agent, i.e., so as to increase the rate at which the agent permeates into and through the skin. A "permeation enhancer" is a material which achieves such permeation enhancement, and a "penetration enhancing amount" of an enhancer as used herein means an amount effective to enhance skin penetration of a selected agent to a desired degree, i.e., to effect the desired pharmacologic response.

By "transdermal" drug delivery, applicant is using the term in its conventional sense, i.e., to indicate delivery of a drug by passage through the skin and into the blood stream. By "transmucosal" drug delivery, applicant intends delivery of a drug by passage of a drug through the mucosal tissue into the blood stream. "Topical" drug delivery is used to mean local administration of a topical drug as in, for example, the treatment of various skin disorders. Aspects of the invention which are described in the context of "transdermal" drug delivery, unless otherwise specified, can apply to transmucosal or topical delivery as well. That is, the compositions, systems, and methods of the invention, unless explicitly stated otherwise, should be presumed to be equally applicable with any one of these three modes of drug delivery.

The term "drug" or "pharmacologically active agent" as used herein is intended to mean a compound or composition of matter which, when administered to an organism (human or animal) induces a desired pharmacologic and/or physiologic effect by local and/or systemic action. In general, the terms include the therapeutic or prophylactic agents in all major therapeutic or prophylactic areas of medicine. Examples of drugs useful in conjunction with the present invention include: anti-infectives such as antibiotics and antiviral agents; analgesics and analgesic combinations; anorexics; antihelminthics; antiarthritics; antiasthmatic agents; anticholinergic agents; anticonvulsants; antidepressants; antidiabetic agents; antidiarrheals; antihistamines; antiinflammatory agents, antimigraine preparations; antimotion sickness drugs; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; steroids; hypnotics; immunosuppressives; muscle relaxants; parasympatholytics; psychostimulants; sedatives; and tranquilizers. For purposes of the aforementioned definition, "drugs" as used herein also include locally administered topical medicaments such as antibacterial agents, antifungals, antimicrobials, cutaneous growth enhancers, antipsoriatics, anti-acne medicaments, and the like.

"Carriers" or "vehicles" as used herein refer to carrier materials without pharmacological activity which are suitable for administration in conjunction with the presently disclosed and claimed compositions, and include any such carrier or vehicle materials known in the art, e.g., any liquid, gel, solvent, liquid diluent, solubilizer, or the like. The carriers and vehicles suitable herein are "pharmaceutically acceptable" in that they are nontoxic, do not interfere with drug delivery, and are not for any other reasons biologically or otherwise undesirable. Examples of specific suitable carriers and vehicles for use herein include water, mineral oil, silicone, inorganic gels, aqueous emulsions, liquid sugars, waxes, petroleum jelly, and a variety of other oils and polymeric materials.

By a "therapeutically effective" amount of a drug or pharmacologically active agent is meant a nontoxic but sufficient amount of the drug or agent to provide the desired therapeutic effect.

The invention is thus, in one embodiment, a method for enhancing the rate of penetration of a pharmacologically active agent through the skin, wherein the method involves co-administration of the agent through a predetermined area of intact skin, and for a predetermined period of time, of the selected agent in a permeation enhancer composition comprising a lower aliphatic ester of a lower aliphatic carboxylic acid and propylene glycol. As used herein, the term "lower" is used to mean a chemical compound having six carbon atoms or less. Preferred materials useful as the lower aliphatic esters have a total of from about three to about six carbon atoms in their esterifying groups plus their acid groups. Thus, typical materials include methyl butrate, methyl proprionate, methyl acetate, ethyl butrate, ethyl propionate, ethyl acetate, propyl butrate, propyl propionate, and propyl acetate. Among these materials, special preference is given to ethyl acetate.

As noted above, the permeation enhancer compositions of the invention also contain a lower alkanol. The lower alkanol can be a monoalkanol such as methanol, ethanol, 1-propanol, 2-propanol or a butanol (n-, i- or t-butanol) or it may be a diol such as propylene glycol. Propylene glycol is particularly preferred.

The enhancers of the invention preferably contain on the order of 35 wt. % to 90 wt. % lower aliphatic ester and approximately 10 wt. % to 65 wt. % lower alkanol. However, the compositions may also include carriers or vehicles as described above, and/or various additional agents and ingredients such as fragrances, pacifiers, preservatives, antioxidants, gelling agents, perfumes, thickening agents, stabilizers, surfactants, emollients, coloring agents, and the like, so long as they are pharmaceutically acceptable and compatible with the selected pharmacologically active agent in the permeation enhancer composition as described above. Particularly preferred additives include hydrophobic co-solvents such as squalene, decylmethylsulfoxide and isopropyl myristate, and surfactants, including anionic, cationic, nonionic and amphoteric surfactants. If such co-solvents or surfactants are present, they will preferentially be included at less than about 15 wt %, preferably less than about 10 wt. % of the total enhancer composition.

While any number of pharmacologically active agents may be administered using the compositions of the present invention, particularly preferred active agents are selected from the group consisting of timolol, captopril, nalbuphine, buprenorphine, and salts thereof. Timolol maleate and captopril are especially preferred.

For timolol maleate, an optimum enhancer formulation contains about 70 wt. % to 90 wt. % lower aliphatic ester and about 10 wt. % to 30 wt. % lower alkanol. In particularly preferred compositions, the lower aliphatic ester is ethyl acetate and the lower alkanol is propylene glycol. For captopril, a preferred enhancer formulation contains about 45 wt. % to 85 wt. % lower aliphatic ester and 15 wt. % to 55 wt. % lower alkanol. Particularly preferred enhancer compositions for use with captopril contain about 50 wt. % to 70 wt. % ethyl acetate, 25 wt. % to 45 wt. % propylene glycol, and 0 wt. % to 15 wt. %, preferably 5 wt. % to 10 wt. %, isopropyl myristate.

The method of delivery of the present compositions may vary, but necessarily involves application of drug and the enhancer composition to a selected intact surface of the skin or other tissue for a period of time sufficient to provide the desired level of drug. The method preferably involves administration of drug and enhancer simultaneously in a single composition, i.e., as an ointment, gel, cream, or the like, or may involve use of a drug delivery device as taught, for example, in U.S. Pat. Nos. 4,849,224, 4,983,395, 4,568,343, 3,797,494, or 3,742,951. The disclosures of each of the aforementioned references are incorporated herein in their entireties, insofar as the devices described therein may be used in conjunction with the present compositions and methods.

When the active agent to be administered with the permeation enhancer as described above is supplied in the form of an ointment, gel, cream or the like, the amount of drug contained within the composition will depend on a variety of factors, including the desired rate of delivery, the desired dosage, the disease to be treated, the nature and activity of the drug, the desired effect, possible adverse reactions, the ability and speed of the drug selected to reach its intended target, and other factors within the particular knowledge of the patient and physician. The amount of enhancer within the total drug/enhancer composition will typically be in the range of 0.1 wt. % to 40 wt. % relative to the total composition.

A transdermal delivery system for the administration of drug and enhancer composition as described herein may take the form of a depot-type device, matrix or laminate-type device, bandages, or the like. A preferred transdermal delivery system for use herein is a laminated composite that contains one or more drug/permeation enhancer reservoirs, a backing layer and, optionally, one or more other layers, e.g., additional drug and/or enhancer reservoirs, release rate controlling membranes, or the like (as those skilled in the art of transdermal delivery will readily appreciate).

In these composites, the backing layer will function as the primary structural element of the device and provide the device with much of its flexibility. This layer also serves as a protective covering to prevent loss of drug and enhancer via transmission through the upper surface of the device. The backing layer may also be used to impart the device with a desirable or necessary degree of occlusivity which in turn causes the area of skin on which the device is placed to become hydrated. The backing is preferably made of a sheet or film of a flexible elastomeric material. Suitable, flexible elastomeric materials include polyether block amide copolymers, polyurethanes, silicone elastomers, rubber-based polyisobutylene, styrene, polyethylene, polypropylene, polyesters, or the like. The preferred polymer used for the backing will depend primarily on the particular pharmacologically active agent incorporated into the device.

The drug reservoir layer comprises an adhesive polymer which is preferably but not necessarily of a material in which the selected drug or vehicle has moderate solubility and diffusivity. Examples of suitable polymeric materials which may be used for the drug reservoir layer include polysiloxanes, polyacrylates, polyurethanes and tacky rubbers.

As alluded to above, the device may also include a release rate controlling means placed in the flow path of the pharmacologically active agent from the reservoir layer to the skin. The rate controlling means will normally be a rate-controlling membrane formed from, e.g., low density polyethylene, ethylene-vinyl acetate copolymers, or the like. A release rate-controlling membrane is particularly preferred for administering captopril.

Prior to use, the laminated composite also includes a release liner layer. Just prior to use, this layer is removed from the device to expose the basal surface of the device. The release liner will normally be made from a drug/enhancer impermeable material that is inherently "strippable" or rendered so by techniques such as silicone or fluorocarbon treatment.

Preferred daily dosages obtained with the present methods and systems will, similarly, vary with the drug administered. The targeted daily dosage will depend on the individual being treated, the indication addressed, the length of time the individual has been on the drug, and the like.

The following examples are put forth so as to provide those with ordinary skill in the art with a complete disclosure and description of how to formulate compositions and systems of the invention, and are not intended to limit the scope of what the inventors regard as their invention. Efforts have been made to ensure accuracy with respect to numbers used (e.g., amounts, temperatures, etc.), but some experimental errors and deviations should be allowed for. Unless indicated otherwise, parts are parts by weight, temperatures are in degrees Centigrade, and pressure is at or near atmospheric.

EXAMPLE 1

Skin Permeability Studies: Timolol Maleate

Methods and Materials

A system employing nine glass Franz diffusion cells was used for the permeability experiments. The cells were modified with inlet and outlet receiver ports to allow continuous flow through the cells. The human cadaver skin used in the experiments was excised from the abdomen area of 50-80 year olds within 12 hours post-mortem at a thickness ranging from 150-600 $\mu$m. The skin was stored frozen for no more than two weeks. The skin was then thawed, cut to circular pieces of approximately 5.0 cm$^2$, soaked in phosphate-buffered isotonic saline for one hour, gently matted dry, and placed on the cells, epidermis side up, to equilibrate for one hour, with a glass cell cap clamped above.

The surface area exposed to the donor phase was 0.5 cm$^2$. The donor vehicles were prepared by saturating timolol maleate ("TM"; obtained from Interchem Corp., Paramus, NJ) in the different enhancer mixtures at 25 wt. % to ensure a constant driving force. The suspensions were stirred overnight. At the start of the experiment, 325 $\mu$l of the saturated mixture was pipetted through the cell cap directly onto the skin, and the cap sealed with a glass stopper.

The receptor phase, in contact with the underside of the skin, was phosphate-buffered (0.1 M, pH 7.4) isotonic saline with 0.05% sodium azide added to prevent bacterial growth. The cells were maintained at 37° C. by circulating thermostatically controlled water through a jacket surrounding the cell body.

Receptor phase solution was pumped through the diffusion cells by means of a Manostat Cassette Pump drive unit. A fraction collector was used to collect the cell effluent. The flow rate was set so that drug concentration in the receptor phase remained well below saturation; a typical flow rate was 5 ml/hr. Uniform mixing of the drug in the receptor phase was achieved by a small magnetic stirring bar driven by an external 600 rpm motor. Fractions were collected at regular intervals and analyzed for timolol using HPLC. Each donor vehicle formulation was tested in triplicate and the 24-hour cumulative drug deliveries averaged for the three cells.

Timolol concentration in the receptor phase was measured using HPLC. No sample pretreatment was required. The HPLC analyses were performed on a Waters 840 system consisting of two Model 510 pumps, a Model 481 UV detector, a Model 710 B WISP (sample processor), and a Digital Computer Model 350 microprocessor/programmer. The column used was a 4.6 mm x 25 cm Whatman ODS-3 Partisil C-18. Timolol was measured using a mobile phase of 0.05 M acetate buffer, pH 3.5/90% acetonitrile (10% acetate buffer) [30/70] at a flow rate of 1.8 ml/min. Absorbance monitoring was at 295 nm, and the retention time found to be 5.3 min.

Results

The goal of this experimentation was to find enhancer compositions capable of enhancing the flux of timolol maleate through human skin such that a therapeutically effective plasma level could be reached. A minimum target flux of 7.5 $\mu$g/cm$^2$/hr was calculated, for a 30 cm$^2$ patch. This flux corresponds to a cumulative delivery of 180 $\mu$g/cm$^2$.

The enhancer compositions tested are listed in Table 1. The flux from neat ethanol (EtOH) and propylene glycol (PG) was found to be well below the target flux when using human skin. The average cumulative amount of TM delivered from EtOH was 29 $\mu$g/cm$^2$ while that from PG was undetectable over 24 h (no TM measured in the receptor phase). Azone ® (5% in PG) gave a cumulative amount delivered of 1.4 $\mu$g/cm$^2$, or over 100 times less than the minimum cumulative amount required.

When ethyl acetate (EtAc) was tested neat the average cumulative amount delivered was found to be about 120 $\mu$g/cm$^2$ still below the minimum target of 180 $\mu$g/cm$^2$ Addition of EtOH to EtAc did not lead to an increase in flux over that of EtAc. However, surprisingly, when PG was added to EtAc at a volume fraction of 0.2, the flux increased well above that found from neat EtAc, i.e., by about threefold. Various mixtures of PG in EtAc were tested and it was found that the 0.8:0.2 mixture of EtAc/PG was the optimum (see FIG. 1). Several other cosolvents were also tested with EtAc (polyethylene glycol 400, oleyl alcohol, squalene, glycerol monooleate, isopropyl myristate).

The remainder of the experiments were directed at enhancing the flux still further by addition of a small amount of a hydrophobic co-solvent. The data from these experiments have been normalized to that from the EtAc/PG (0.8:0.2) (see Table 2).

TABLE 1

| Solvent system | Cumulative Amount Permeating ($\mu$g/cm$^2$) | Relative Amounts* |
|---|---|---|
| EtOH | 29 | 0.05 |
| EtOH/EtAc (0.2:0.8) | 52 | 0.10 |
| PG | 0 | 0 |
| PG/EtAc (0.25:0.75) | 2.9 | 0.005 |
| PG/EtAc (0.50:0.50) | 56 | 0.10 |

TABLE 1-continued

| Solvent system | Cumulative Amount Permeating (μg/cm²) | Relative Amounts* |
|---|---|---|
| PG/EtAc (0.20:0.80) | 550 | 1 |
| EtAc | 172 | 0.31 |
| PG/Azone ® (0.95:0.05) | 1.4 | 0.003 |
| EtAc/PEG 400 (0.95:0.05) | 61 | 0.11 |
| EtAc/PEG 400 (0.80:0.20) | 19 | 0.03 |
| EtAc/oleyl alcohol (0.95:0.05) | 229 | 0.41 |
| EtAc/squalene (0.95:0.05) | 290 | 0.53 |
| EtAc/GMO** (0.80:0.20) | 434 | 0.78 |
| EtAc/isopropyl myristate (0.95:0.05) | 266 | 0.48 |
| EtAc/isopropyl myristate (0.80:0.20) | 196 | 0.36 |

*Relative to the average flux of TM through human skin from EtAc/PG (0.80:0.20)
**Glycerol monooleate

TABLE 2

| Solvent System | Relative Amount Delivered |
|---|---|
| EtAc/PG/squalene (0.75:0.20:0.05) | 1.07 |
| EtAc/PG squalene (0.80:0.10:0.10) | 0.59 |
| EtAc/PG/squalene (0.45:0.50:0.05) | 0.14 |
| EtAc/PG/squalene (0.0.79.5:0.20:0.05) | 1.0 |
| EtAc/PG/squalene (0.79:0.20:0.01) | 1.14 |
| EtAc/PG/squalene (0.77.5:0.20:0.025) | 1.03 |
| EtAc/PG/oleyl alcohol (0.75:0.20:0.05) | 0.19 |
| EtAc/PG/decyl methyl sulfoxide (0.79:0.20:0.05) | 0.43 |
| EtAc/PG/H₂O (0.75:0.20:0.05) | 0.27 |
| EtAc/PG/glycerol monooleate (0.75:0.20:0.05) | 1.29 |
| EtAc/PG/Tween 20 (0.75:0.20:0.05) | 1.44 |
| EtAc/PG/Tween 80 (0.75:0.20:0.05) | 0.58 |
| EtAc/PG/mineral oil (0.75:0.20:0.05) | 0.94 |

EXAMPLE 2

Skin Permeability Studies: Buorenorohine

The methodology of the preceding example was used to evaluate the skin permeability of the narcotic analgesic, buprenorphine. Various mixtures of EtAc and PG as flux enhancers were evaluated. The total cumulative amount of buprenorphine permeating human skin from the enhancer vehicles is shown in Table 3. In the experiment summarized in Table 3, all vehicles were saturated with excess solid buprenorphine containing excess solid drug; n=3 to 6. The skin was obtained from cadavers and frozen (one to two weeks) before use in the experiments. In all cases, the skin was removed from the abdomen. The abbreviations used in Table 3 are as follows: "DMS" is decylmethylsulfoxide; and "OcAc" is octylacetate.

TABLE 3

Relative Cumulative Amount of Buprenorphine Delivered Through Human Skin In Vitro From Various Vehicles

| Vehicle | Cell Size (cm²) | Donor Volume (μL) | Total BN Delivered (μg/cm²) |
|---|---|---|---|
| EtAc | 0.65 | 325 | 5.0* |
| pG | 0.65 | 325 | 8.6 |
| EtOH | 0.65 | 325 | 15 |
| EtAc/PG (0.80:0.20) | 0.65 | 325 | 15* |
| EtAc/PG (0.50:0.50) | 0.65 | 325 | 20 |
| EtAc/PG (0.25:0.75) | 0.65 | 325 | 4.0 |
| EtAc/PG/DMS (0.75:0.20:0.05) | 0.65 | 325 | 25 |
| EtAc/PG/Tween 20 (0.75:0.20:0.05) | 0.65 | 325 | 24 |
| EtAc/PG/Tween 80 (0.75:0.20:0.05) | 0.65 | 325 | 22 |
| EtAc/PG/Span 80 (0.75:0.20:0.05) | 0.65 | 325 | 12 |
| EtAc/PG/Pluronic L31 (0.75:0.20:0.05) | 0.65 | 325 | 19 |
| EtAc/PG/MO (0.75:0.20:0.05) | 0.65 | 325 | 17** |
| EtAc/PG/MO (0.79:0.20:0.01) | 0.65 | 325 | 6.0 |
| EtAc/PG/SL (0.75:0.20:0.05) | 0.65 | 325 | 26 |
| EtAc/PG/OcAcg (0.75:0.20:0.05) | 0.65 | 325 | 5.0 |
| EtAc/PG/IPM** (0.75:0.20:0.05) | 0.65 | 325 | 4.0 |

*n = 15; skin from 5 donors used in these experiments.
**n = 9; skin from 3 different donors.

Figure 2:
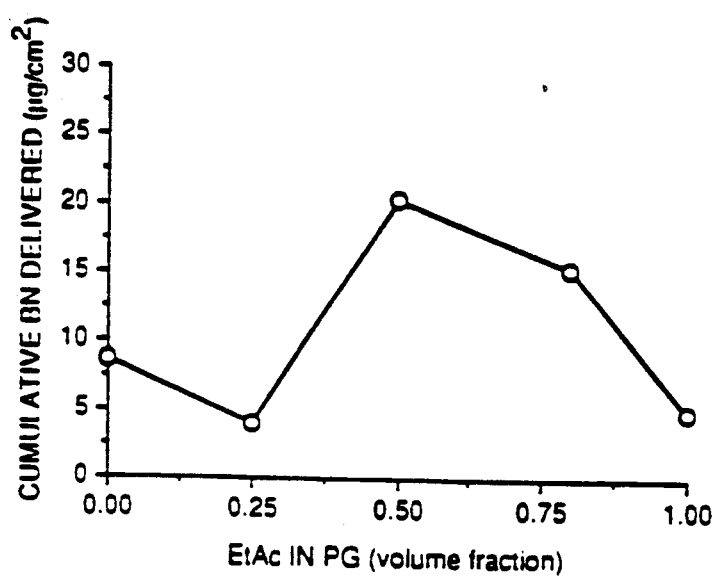
FIG. 2 graphically illustrates the cumulative amount of buprenorphine permeating through human skin over a 24 hour period using the enhancer compositions of the invention, as described in Example 2.

A plot of the total amount permeating over 24 hours versus the volume fraction of EtAc and PG is shown in FIG. 2. As with timolol maleate, mixtures of EtAc and PG (0.50:0.50 and 0.80:0.20) appear to achieve a maximum degree of enhancement. The 80:20 vehicle was tested on five different skin donors, each with an n of 3. The low average for one skin type was about 4 μg/cm², while the high average was 28 μg/cm² The mean of all the skin types was 15 μg/cm2 Compared with timolol maleate, permeation by buprenorphine was somewhat more variable.

Figure 3:
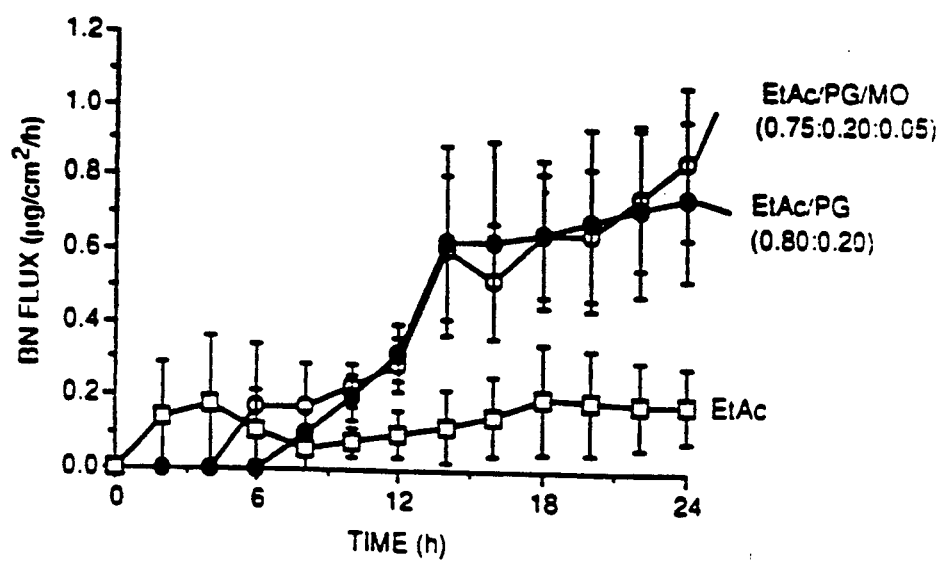
FIG. 3 graphically illustrates the flux of buprenorphine through human cadaver skin from various vehicles, also as described in Example 2.
Figure 4:
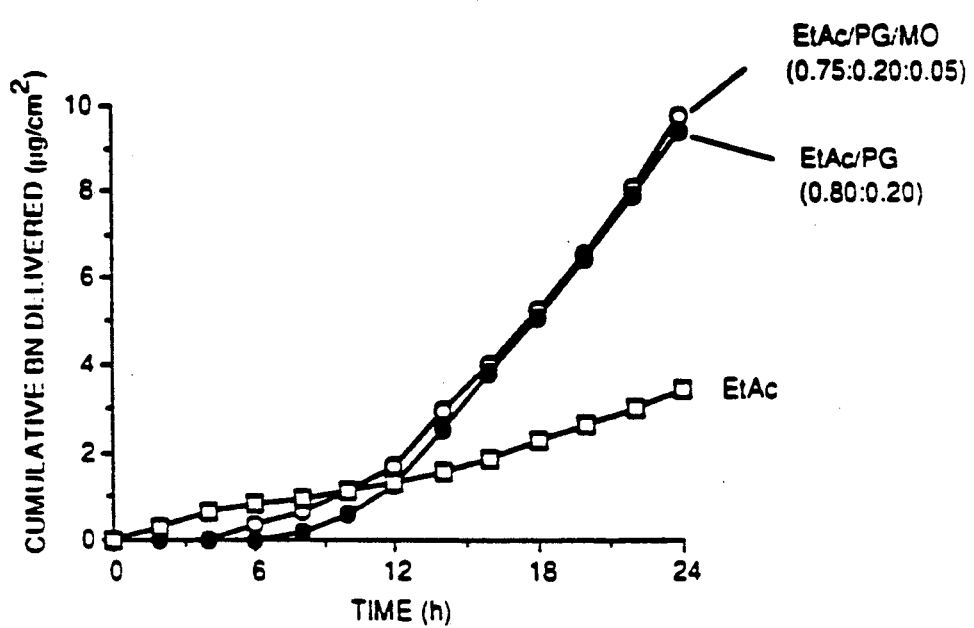
FIG. 4 illustrates the cumulative amount of buprenorphine permeating through human cadaver skin from various vehicles, also as described in Example 2.
Figure 5:
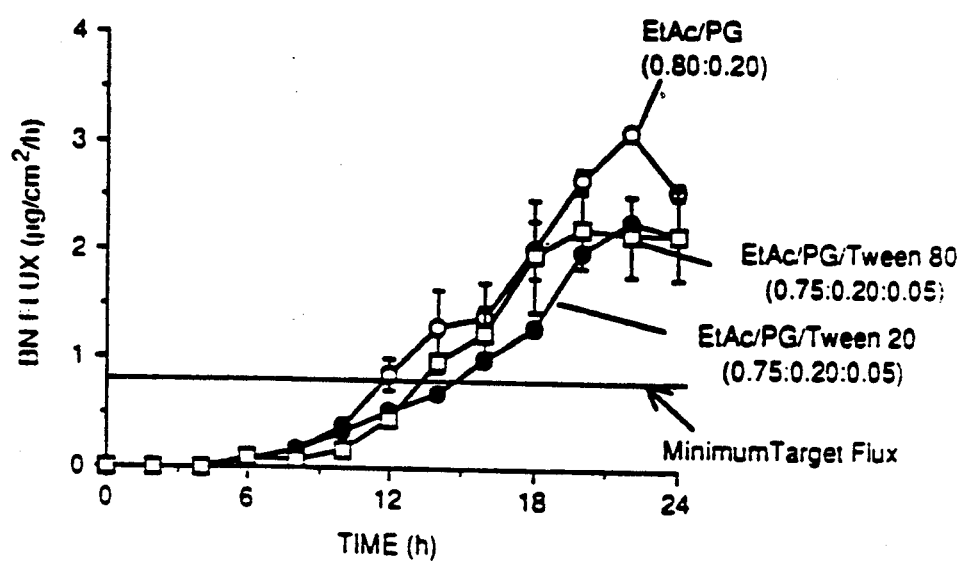
FIG. 5 and 6 are similar to FIGS. 3 and 4, but illustrate the results with enhancer compositions of the invention containing various hydrophobic co-solvents, as explained in Example 2.
Figure 6:
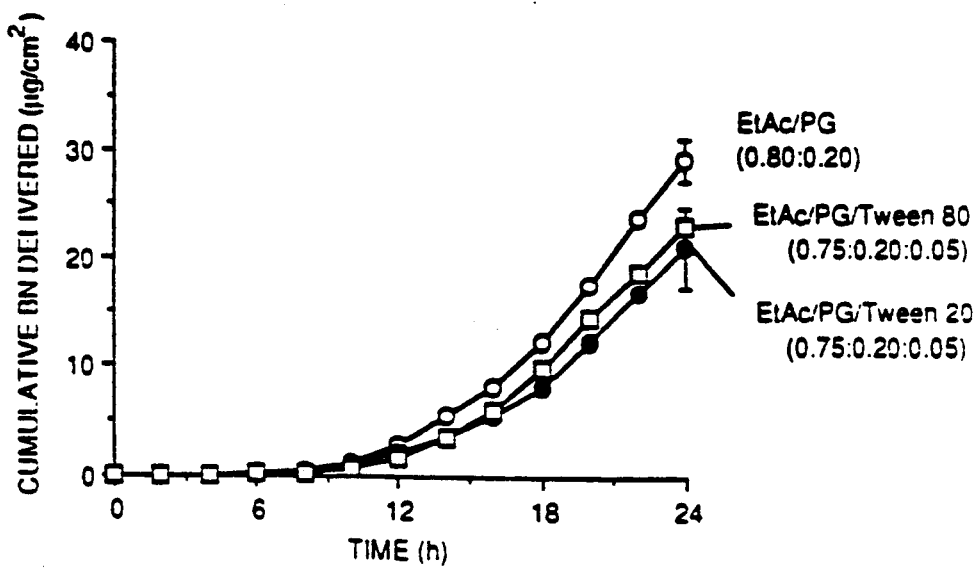

The incorporation of hydrophobic co-solvent materials into the drug/enhancer composition was also evaluated. Some of these co-solvents, including Tween-20, Tween-80, decyl methyl sulfoxide (DMS) and squalene raised the buprenorphine permeation rate above about 20 μg/cm² over 24 hours. All were added at a volume fraction of 0.05 to EtAc/PG (0.75:0.20). FIG. 3 graphically shows the flux of buprenorphine through human cadaver skin from various vehicles, with an active surface area of 0.65 cm². FIG. 4 graphically represents the cumulative amount of buprenorphine permeating human cadaver skin from various vehicles, again with an active surface area of 0.65 cm² FIGS. 5 and 6 are similar to the foregoing, but illustrate the results with various hydrophobic cosolvents.

EXAMPLE 3

Skin Permeability Studies: Captopril

Figure 7:
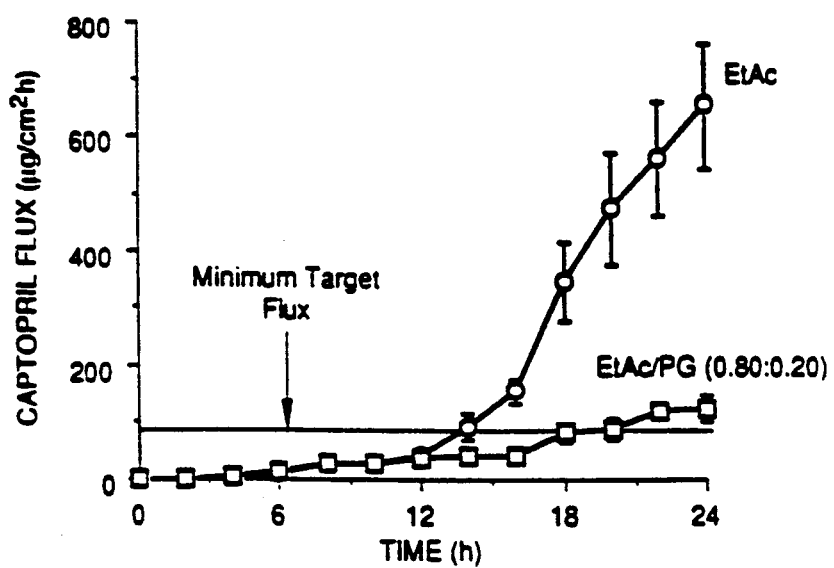
FIGS. 7 and 8 graphically illustrate the flux of captopril through human skin using enhancer compositions formulated according to the invention, as described in Example 3.
Figure 8:
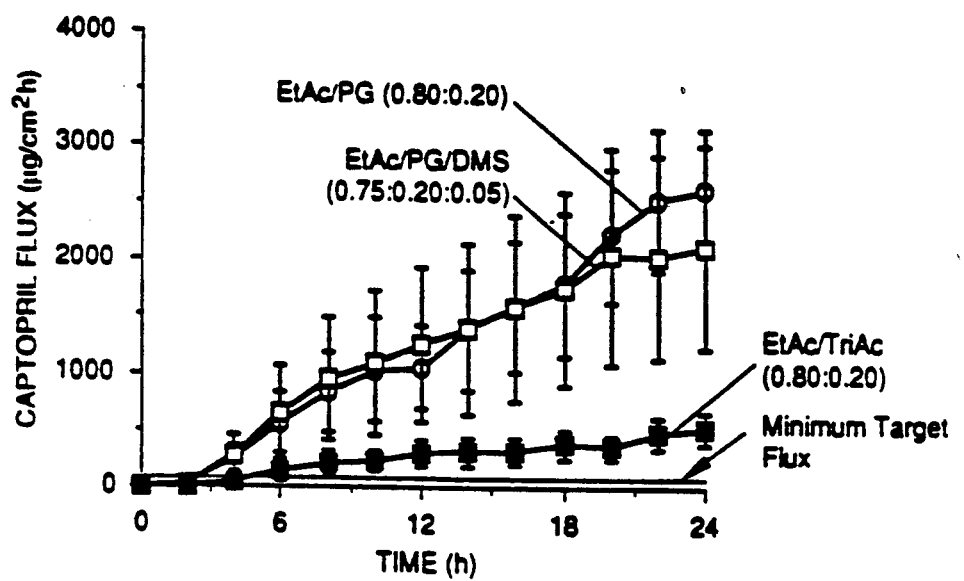

The flux of captopril through human skin from saturated solutions of EtAc and EtAc/PG (0.80:0.20) was evaluated as in the preceding example. Results are shown graphically in FIG. 7. As may be seen in the FIGURE, the minimum target flux was met or exceeded substantially. This experiment was repeated using EtAc/PG (0.80:0.20) and the additional vehicles EtAc/DMS (0.80:0.20) and EtAc/Triaceton (0.80:0.20). The results, as graphically summarized in FIG. 8, showed extremely high transdermal fluxes from all of the vehicles. For the EtAc/PG and EtAc/DMS vehicles, the flux of captopril was about 30 times the minimum target flux.

EXAMPLE 4

Further Captopril Studies

Additional in vitro permeability studies were carried out with captopril using a variety of enhancer compositions. The results of these tests are set forth in Table 4. In the table, "Jojoba" represents jojoba oil, "IPM" represents isopropyl myristate, "S.D." represents standard deviation, and "A.D." represents average deviation (i.e., the average value for N=2), with other abbreviations as defined earlier. All samples tested were abdomen skin unless otherwise indicated. Samples designated "Elvax" (an ethylene-vinyl acetate copolymer available from E.I. duPont de Nemours and Co.) were used to test the polymeric membrane alone, while samples designated "Skin/Elvax" were used to evaluate the combination of the polymeric membrane with skin. As may be deduced from the table, a number of enhancer compositions containing two or more components provided for a significantly higher flux relative to that obtained with single component enhancers; the addition of isopropyl myristate, in particular, gave rise to a far higher flux than that obtained in its absence. (Note: in experiment #4-12, no flux was seen before 16 hours in 8 of 9 cells. This led to the conclusion that captopril was forming a disulfide with itself, meaning that the captopril flux has been underestimated in experiments 4-1 through 4-12. After experiment #4-14, 0.001M citric acid and EDTA were used in the receptor phase to prevent the formation of the disulfide. Experiment 4-13 used citric acid, but experiment 4-14 used ascorbic acid.

TABLE 4

| Experiment | Composition of Vehicles Used | Skin Sample (Abdomen) | 24 hr Flux ($\mu g/cm^2/hr$) Mean | S.D. or A.D. | 24 hr Flux ($\mu g/cm^2/hr$) Mean | S.D. or A.D. |
|---|---|---|---|---|---|---|
| 4-1 | PG | 91-15 | 157 | N = 1 | 1481 | N = 1 |
|  | EA |  | 655 | 111 | 4795 | 859 |
|  | EA/PG (80:20) |  | 124 | 23.7 | 1200 | 199 |
| 4-2 | EA/PG (80:20) | 91-24 | 2603 | 553 | 31630 | 9785 |
|  | EA/PG/DMS (79:20:1) |  | 2113 | 887 | 30160 | 14960 |
|  | EA/Triacetin (80:20) |  | 526 | 138 | 6631 | 2292 |
| 4-3 | PG | 91-23 | No peaks |  | No peaks |  |
|  | EA |  |  |  |  |  |
|  | EA/PG/Jojoba (75:20:5) |  |  |  |  |  |
| 4-4 | EA | 90-231 | 22.3 | 17.2 | 197.5 | 27.7 |
|  | EA/PG (80:20) |  | 33.9 | 9.8 | 417.7 | 138.1 |
|  | PG |  | 3.4 | 3 | 54.9 | 40.6 |
| 4-5 | EA/PG (80:20) | 90-231 | 26.8 | There was | 301.6 |  |
|  | EA/PG (80:20) | 91-24 | 2471 | an N = 1 for | 37829 |  |
|  | EA/PG (80:20) | 91-27 | 1078 | all these. | 16930 |  |
|  | EA/PG (80:20) | Thigh 14384 | 103.2 |  | 845.8 |  |
|  | EA/PG (80:20) | Abd 29980 | 10 | No S.D. | 207.4 |  |
|  | EA/PG (80:20) | 90-197 | 273.6 |  | 2212 |  |
|  | EA/PG (80:20) | 91-30 | 99.2 |  | 960.4 |  |
|  | EA/PG (80:20) | 90-243 | 60.2 |  | 625.3 |  |
|  | EA/PG (80:20) | Back 14386 | 60.2 |  | 414.4 |  |
| 4-6 | EA/PG (80:20) | 91-57(1) | 29.3 | 16.4 | 302 | 196 |
|  | EA/PG (60:40) |  | 26.3 | 7.6 | 561.8 | 440.3 |
|  | EA/PG (25:75) |  | 49.3 | 11.4 | 591.4 | 179.6 |
| 4-7 | EA/PG (80:20) | 91-57(4) | 275.6 | 24 hr. Values | 2925 | 24 hr Values |
|  | EA/PG/IPM (75:20:5) |  | 194.8 | Estimated | 1390 | Estimated |
|  | EA/PG/IPM (55:40:5) |  | 662 | No S.D. | 7021 | No S.D. |
| 4-8 | EA/EtOH (80:20) | 91-57 | 23.7 | 8.4 | 143.3 | 59.1 |
|  | EA/EtOH (50:50) |  | 49.2 | 38 | 370.2 | 324.2 |
|  | EA/EtOH (25:75) |  | 20.9 | 24.1 | 153.4 | 177.8 |
| 4-9 | EA/PG (80:20) | 91-57(1) | 82.1 | 17.8 | 938.4 | 207.8 |
|  | EA/PG/IPM (55:40:5) |  | 216.9 | 110.6 | 1842 | 859.9 |
|  | EA/PG (60:40) |  | 46.1 | 10.2 | 489.3 | 45.8 |
| 4-10 | EA/PG/IPM (35:60:5) | 91-57(2,4) | 718.2 | 165 | 5285 | 1812 |
|  | EA/PG (40:60) | 91-57(2,4) | 70.6 | 10.4 | 576.8 | 166.6 |
|  | EA/PG (80:20) | 91-57(2) | 162.8 | N = 1 | 1308 | N = 1 |
|  | EA/PG/IPM (55:40:10) | 91-57(2) | 768.8 | 396 | 7779 | 3108 |
| 4-11 | EA/PG/IPM (25:74:1) | 91-57(3) | 56.8 | 59 | 412.6 | 425.9 |
|  | EA/PG/IPM (35:64:1) |  | 161.4 | 107.1 | 1165 | 913.6 |
|  | EA/PG (80:20) |  | 76.6 | 32.4 | 600 | 318.8 |
| 4-12 | EA/PG/IPM (55:40:5) | Various |  |  |  |  |
| 4-13 | EA/PG/IPM (55:40:5) | 91-58 | 1836 | 1158 | 16526 | 12214 |
| 4-14 | EA/PG/IPM (55:40:5) | 91-12 | 362 | 40 | 2441 | 424 |
|  | (Uses ascorbic acid in place of citric acid: not as effective) | 91-58 | 1401 | 194 | 10201 | 1569 |
| 4-15 | EA/PG/IPM (55:40:5) | 91-58 | 1772 | 446 | 16929 | 4391 |
|  | EA/PG (80:20) | 91-58 | 658 | 281 | 6004 | 2885 |
|  | EA/PG (80:20) | Elvax 250 | 77 | 30 | 4068 | 1080 |
| 4-16 | EA/PG/IPM (55:40:5) | Elvax 250 | 74 | 24 | 3915 | 966 |
|  |  | 91-58 | 2122 | 565 | 22333 | 7369 |
|  |  | Skin/Elvax | 263 | 91 | 5064 | 1246 |
| 4-17 | EA/PG/IPM (55:40:5) | Elvax 250 | 113 | 40 | 5311 | 2385 |
|  |  | 90-197 | 2968 | 724 | 30751 | 11671 |
|  |  | Skin/Elvax | 149 | 25 | 3710 | 189 |
| 4-18 | EA/PG/IPM (55:40:5) | Elvax 40 | 1823 | 2172 | 339340 | 28025 |
|  |  | 91-58 | 2315 | 462 | 26580 | 8766 |
|  |  | Skin/Elvax | 499 | 99 | 7294 | 328 |
| 4-19 | EA/PG/IPM (55:40:5) | Elvax 40 | 177 |  | 357692 |  |

TABLE 4-continued

| Experiment | Composition of Vehicles Used | Skin Sample (Abdomen) | 24 hr Flux (μg/cm²/hr) Mean | 24 hr Flux (μg/cm²/hr) S.D. or A.D. | 24 hr Flux (μg/cm²/hr) Mean | 24 hr Flux (μg/cm²/hr) S.D. or A.D. |
|---|---|---|---|---|---|---|
|  | Thigh skin used. One cell each. | 90-264 Skin/Elvax | 58 33 |  | 2361 1006 |  |
| 4-20 | EA/PG/IPM (55:40:5) | Elvax 450 91-58 Skin/Elvax |  |  |  |  |
| 4-21 | EA/PG/IPM (55:40:5) | Elvax 40 91-58 Skin/Elvax | 295 1890 367 | 243 525 2 | 249869 17284 4855 | 208406 3899 491 |

EXAMPLE 5

Preparation of Transdermal Patches

Transdermal patches containing the enhancer compositions of the invention and the pharmacologically active agent to be administered were prepared as follows. Paper liner was cut into a 10×14 cm width; the paper was #1360, #72, obtained from 3M corporation, coated on both sides with polyethylene, with one side also coated with silicone for release of adhesive. Transfer adhesive (#9871, pressure-sensitive acrylate adhesive developed by 3M) was cut into a shape similar to that of the paper liner and the adhesive liner was then transferred to the paper liner. A 2.2 cm i.d. hole was cut in the adhesive-coated paper liner using a punch and die apparatus. The adhesive was peeled off and transferred onto the polyethylene-coated side of the backing film (Scotch pack 1009). The sandwich was cut into a rectangle using a brass template, and then cut into a 3.9 cm i.d. circle using a 3.9 cm die and punch apparatus. The reservoir material (Santara No. 8100, DuPont) was cut into a 2.0 cm² circles using a tap and hammer. These pieces were washed for 48 hours in a soxhlet extracting apparatus. Triple layer thick sandwiches were prepared by heat sealing three individual pieces together one at a time at 240° C. for 20 seconds. The reservoir was then heat sealed onto the polyethylene-coated foil at 170° C. for 20 seconds. The patches were loaded by immersion into a saturated solution containing the desired drug to be incorporated therein. The 2.0 cm² patches were loaded so as to contain approximately 300 μl total liquid.

EXAMPLE 6

Delivery of Drugs In Vivo From Transdermal Patches

Transdermal patches prepared using the methodology of the preceding example were made with timolol maleate. The patches were placed on the shaved dorsal side of New Zealand white rabbits (n=4). Blood samples were withdrawn from the ear at various times over a 48 hour period following application of the patches. The patches were removed after 24 hours and the irritation induced by the patches was measured. The plasma levels were reasonably high over the first four hours of the experiment, 230 ng/ml. However, by 24 hours, the plasma levels were very low. This result was expected because of the very high skin permeability of rabbit skin toward the solvent used as compared with human skin. A very conservative estimate for the difference in flux is fivefold. Skin irritation using these patches was evaluated using the Draize method of evaluation (G.H. Draize et al., *J. Pharmacol. Exp. Ther.*, 82:377 (1944)). Table 4 shows the scoring system used: erythema is the redness at the site of application and edema is swelling (as determined by the raising of the skin relative to the adjacent skin). For delivery systems without drug, four devices were applied on the dorsal side of the rabbits' backs (n=4).

TABLE 5

| Draize Scoring of Irritation From Topically Applied Substances* | |
|---|---|
| Erythema (and Eschar) Formation | |
| No erythema | 0 |
| Very slight erythema (barely perceptible) | 1 |
| Well-defined erythema | 2 |
| Moderate to severe erythema | 3 |
| Severe erythema (beet redness) to slight eschar formation (injury in depth) | 4 |
| Edema Formation | |
| No edema | 0 |
| Very slight edema (barely perceptible) | 1 |
| Slight edema (edges of area well-defined by definite raising) | 2 |
| Moderate edema (raised approximately 1 mm) | 3 |
| Severe edema (raised more than 1 mm extending beyond the area of exposure) | 4 |

*Total possible score is 4 for either erythema or edema; cumulative index (combined erythema and edema) has a total possible score of 8.

We claim:

1. A method for enhancing the rate of penetration of a pharmacologically active agent through the skin, comprising applying to a selected area of intact skin: (a) a therapeutically effective amount of a pharmacologically active agent selected from the group consisting of timolol, captopril, nalbuphine, buprenorhpine, and salts thereof; and (b) a permeation enhancer composition comprising (i) approximately 35 wt. % to 90 wt. % of a lower aliphatic ester of a lower aliphatic carboxylic acid, containing a total of from three to six carbon atoms; (ii) approximately 10 wt. % to 65 wt. % of a lower alkanol; and (iii) 0 wt. % to approximately 15 wt. % of an additional permeation enhancing component selected from the group consisting of squalene, decylmethyl sulfoxide, isopropyl myristate, and surfactant.

2. The method of claim 1, wherein the permeation enhancer composition contains approximately 35 wt. % to 90 wt. % lower aliphatic ester and 10 wt. % to 65 wt. % lower alkanol.

3. The method of claim 1, wherein the lower aliphatic ester is selected from the group consisting of methyl butrate, methyl propionate, methyl acetate, ethyl butrate, ethyl propionate, ethyl acetate, propyl butrate, propyl propionate and propyl acetate, and the lower alkanol is selected from the group consisting of methanol, ethanol, 1-propanol, 2-propanol, n-butanol, i-butanol, t-butanol, propylene glycol, ethylene glycol, and glycerin.

4. The method of claim 3, wherein the lower aliphatic ester is ethyl acetate and the lower alkanol is propylene glycol.

5. The method of claim 1, wherein the pharmacologically active agent is selected from the group consisting of timolol, captopril, nalbuphine, buprenorphine, and salts thereof.

6. The method of claim 1, wherein the pharmacologically active agent and the permeation enhancer composition are present in a single pharmaceutical composition, and wherein the composition further includes a pharmaceutically acceptable inert vehicle.

7. The method of claim 1, wherein the permeation enhancer composition further includes at least one additional permeation enhancing component.

8. The method of claim 7, wherein the at least one additional permeation enhancing component is selected from the group consisting of squalene, decylmethylsulfoxide and isopropyl myristate.

9. The method of claim 7, wherein the at least one additional permeation enhancing component is a surfactant.

10. A method for enhancing the rate of penetration of timolol maleate through the skin, comprising applying to a selected area of intact skin: (a) a therapeutically effective amount of timolol maleate; and (b) a permeation enhancer composition comprising approximately 70 wt. % to 90 wt. % ethyl acetate and 10 wt. % to 30 wt. % propylene glycol.

11. A method for enhancing the rate of penetration of captopril through the skin, comprising applying to a selected area of intact skin: (a) a therapeutically effective amount of captopril; and (b) a permeation enhancer composition comprising 50 wt. % to 70 wt. % ethyl acetate, 25 wt. % to 45 wt. % propylene glycol, and up to 15 wt. % isopropyl myristate.

12. The method of claim 11, wherein the permeation enhancer composition contains isopropyl myristate in an amount up to about 10 wt. %.

13. A composition of matter for the transdermal administration of a pharmacologically active agent, comprising: (a) a therapeutically effective amount of a pharmacologically active agent selected from the group consisting of timolol, captopril, nalbuphine, buprenorphine, and salts thereof; and (b) a permeation engancer composition comprising (i) approximately 35 wt. % to 90 wt. % of a lower aliphatic ester of a lower aliphatic carboxylic acid, containing a total of from three to six carbon atoms; and (ii) approximately 10 wt. % to 65 wt. % of a lower alkanol; and (iii) 0 wt. % to approximately 15 wt. % of an additional permeation enhancing component selected from the group consisting of squalene, decylmethyl sulfoxide, isopropyl myristate, and surfactant.

14. The composition of claim 13, comprising approximately 35 wt. % to 90 wt. % lower aliphatic ester and 10 wt. % to 65 wt. % lower alkanol.

15. The composition of claim 13, wherein the lower aliphatic ester is selected from the group consisting of methyl butrate, methyl propionate, methyl acetate, ethyl butrate, ethyl propionate, ethyl acetate, propyl butrate, propyl propionate and propyl acetate, and the lower alkanol is selected from the group consisting of methanol, ethanol, 1-propanol, 2-propanol, n-butanol, i-butanol, t-butanol, propylene glycol, ethylene glycol, and glycerin.

16. The composition of claim 15, wherein the lower aliphatic ester is ethyl acetate and the lower alkanol is propylene glycol.

17. The composition of claim 13, wherein the pharmacologically active agent is selected from the group consisting of timolol, captopril, nalbuphine, buprenorphine, and salts thereof.

18. The composition of claim 13, further including a pharmaceutically acceptable inert vehicle.

19. The composition of claim 13, wherein the permeation enhancer composition further includes at least one additional permeation enhancing component.

20. The composition of claim 19, wherein the at least one additional permeation enhancing component is selected from the group consisting of squalene, decylmethylsulfoxide and isopropyl myristate.

21. The composition of claim 19, wherein the at least one additional permeation enhancing component is a surfactant.

22. A composition for administering timolol maleate transdermally, comprising: (a) a therapeutically effective amount of timolol maleate; and (b) a permeation enhancer composition comprising approximately 70 wt. % to 90 wt. % ethyl acetate and 10 wt. % to 30 wt. % propylene glycol.

23. A composition for administering captopril transdermally, comprising: (a) a therapeutically effective amount of captopril; and (b) a permeation enhancer composition comprising 50 wt. % to 70 wt. % ethyl acetate, 25 wt. % to 45 wt. % propylene glycol, and up to about 15 wt. % isopropyl myristate.

24. The composition of claim 23, wherein the permeation enhancer composition contains up to about 10 wt. % isopropyl myristate.

25. A laminated composite for administering a pharmacologically active agent through a selected area of skin over a sustained time period, comprising:
  (a) a backing layer that is substantially impermeable to the pharmacologically active agent;
  (b) a reservoir layer comprising an adhesive polymer and defining the basal surface of the device for adhering to the skin;
  (c) a therapeutically effective amount of pharmacologically active agent selected from the group consisting of timolol, captopril, nalbuphine, buprenorphine, and salts thereof; and
  (d) a permeation enhancer composition comprising (i) approximately 35 wt. % to 90 wt. % of a lower aliphatic ester of a lower aliphatic carboxylic acid, containing a total of from three to six carbon atoms; and (ii) approximately 10 wt. % to 65 wt. % of a lower alkanol; and (iii) 0 wt. % to approximately 15 wt. % of an additional permeation enhancing component selected from the group consisting of squalene, decylmethyl sulfoxide, isopropyl myristate, and surfactant.

26. The method of claim 25, wherein the lower aliphatic ester is selected from the group consisting of methyl butrate, methyl propionate, methyl acetate, ethyl butrate, ethyl propionate, ethyl acetate, propyl butrate, propyl propionate and propyl acetate, and the lower alkanol is selected from the group consisting of methanol, ethanol, 1-propanol, 2-propanol, n-butanol, i-butanol, t-butanol, propylene glycol, ethylene glycol, and glycerin.

27. The method of claim 26, wherein the lower aliphatic ester is ethyl acetate and the lower alkanol is propylene glycol.

28. The laminated composite of claim 25 wherein the adhesive polymer is selected from the group consisting of polysiloxanes, polyacrylates, polyurethanes and tacky rubbers.

29. The laminated composite of claim 25, further comprising a release rate controlling means in the flow path of the pharmacologically active from the reservoir layer to the skin.

30. The laminated composite of claim 29, wherein the release rate controlling means is an ethylene-vinyl acetate, ethylene vinyl acetate organic acid terpolymer, polyamide, polyester; or acrylic resin membranes.

31. The method of claim 25, wherein the pharmacologically active agent is selected from the group consisting of timolol, captopril, nalbuphine, buprenorphine, and salts thereof.

32. A permeation enhancer composition comprising (i) approximately 25 wt. % to 55 wt. % of a lower aliphatic ester of a lower aliphatic carboxylic acid; and (ii) approximately 40 wt. % to 74 wt. % of a lower alkanol; and (iii) up to approximately 1 wt. % to 5 wt. % isopropyl myristate.

* * * * *